(12) United States Patent  
Nair

(10) Patent No.: US 11,596,389 B2  
(45) Date of Patent: Mar. 7, 2023

(54) METHOD FOR MULTI-FREQUENCY IMAGING AND COMPOSITE IMAGE DISPLAY USING HIGH-BANDWIDTH TRANSDUCER OUTPUTS

(71) Applicant: VOLCANO CORPORATION, San Diego, CA (US)

(72) Inventor: Anuja Nair, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 230 days.

(21) Appl. No.: 16/556,296

(22) Filed: Aug. 30, 2019

(65) Prior Publication Data

US 2019/0380686 A1   Dec. 19, 2019

Related U.S. Application Data

(63) Continuation of application No. 14/135,185, filed on Dec. 19, 2013, now Pat. No. 10,398,413.

(Continued)

(51) Int. Cl.
*A61B 8/08* (2006.01)
*A61B 8/12* (2006.01)
(Continued)

(52) U.S. Cl.
CPC .............. *A61B 8/5261* (2013.01); *A61B 8/12* (2013.01); *A61B 8/5246* (2013.01);
(Continued)

(58) Field of Classification Search
CPC ... G06T 7/0012; A61B 8/5246; A61B 8/5238; A61B 8/5253; A61B 8/5261; A61B 8/13;
(Continued)

(56) References Cited

U.S. PATENT DOCUMENTS 5,243,988 A   9/1993 Sieben
5,546,948 A   8/1996 Hamm
(Continued)

OTHER PUBLICATIONS

Katouzian, Amin, Elsa D. Angelini, Stephane G. Carlier, Jasjit S. Suri, Nassir Navab, and Andrew F. Laine. "A state-of-the-art review on segmentation algorithms in intravascular ultrasound (IVUS) images." IEEE Transactions on Information Technology in Biomedicine 16, No. 5 (2012): 823-834.*

(Continued)

*Primary Examiner* — Carolyn A Pehlke

(57) ABSTRACT

A method for imaging a volume within a patient volume is provided. The method includes generating a first signal and a second signal, directing the first signal and the second signal to a spot in the patient volume; receiving a first response signal and a second response signal from the spot in the patient volume; providing a first image from of the patient volume using the first response signal; providing a second image from the patient volume using the second response signal; and combining the first image and the second image to form a composite image. The method includes receiving multiple images at multiple frequency ranges; selecting a region of interest including the plurality of images; selecting multiple border lines separating the region of interest into multiple sub-regions; selecting data from an image in a sub-region; and forming an image in the region of interest.

8 Claims, 12 Drawing Sheets

Related U.S. Application Data

(60) Provisional application No. 61/740,723, filed on Dec. 21, 2012.

(51) Int. Cl.
*A61B 5/00* (2006.01)
*A61B 8/00* (2006.01)

(52) U.S. Cl.
CPC ............ *A61B 5/0066* (2013.01); *A61B 5/0084* (2013.01); *A61B 8/0891* (2013.01); *A61B 8/445* (2013.01)

(58) Field of Classification Search
CPC .. A61B 8/00; A61B 8/12; A61B 8/463; A61B 8/52; A61B 8/085; A61B 8/445
See application file for complete search history.

(56) References Cited

U.S. PATENT DOCUMENTS

| | | | |
|---|---|---|---|
| 6,200,268 B1 | 3/2001 | Vince | |
| 6,641,540 B2 | 11/2003 | Fleischman | |
| 7,175,597 B2 | 2/2007 | Vince | |
| 7,627,156 B2 | 12/2009 | Margolis | |
| 2004/0037455 A1 | 2/2004 | Klingensmith | |
| 2005/0196026 A1 | 9/2005 | Klingensmith | |
| 2011/0087104 A1 | 4/2011 | Moore | |
| 2012/0123271 A1 | 5/2012 | Cai | |
| 2014/0066768 A1* | 3/2014 | Sui | G01S 7/52047 600/443 |

OTHER PUBLICATIONS

Srinivas, Sushma et al "Multiresolution Analysis of Intravascular Ultrasound Harmonic Signals to Image Pre-Rupture Plaques", Ultrasonics Symposium, 2009 IEEE International.

Srinivas, Sushma et al, "Nonlinear Tissue Characterization with Intravascular Ultrasound Harmonic Imaging", Ultrasonics Symposium, 2009 IEEE International.

Hoskins, Peter R. et al "Diagnostic Ultrasound: Physics and Equipment", Cambridge University Press, 2010, Chapters 2,4 and glossary.

* cited by examiner

METHOD FOR MULTI-FREQUENCY IMAGING AND COMPOSITE IMAGE DISPLAY USING HIGH-BANDWIDTH TRANSDUCER OUTPUTS

CROSS-REFERENCE TO RELATED APPLICATIONS

The present application is a continuation of U.S. patent application Ser. No. 14/135,185, filed Dec. 19, 2013, now U.S. Pat. No. 10,398,413, which claims the benefit of U.S. Provisional Patent Application No. 61/740,723, filed Dec. 21, 2012. The entire disclosures of these applications are hereby incorporated by reference. The present application is also related to U.S. Patent Application No. 61/740,822 entitled "Method for Multi-Frequency Imaging Using High-Bandwidth Transducer Outputs," the contents of which are also hereby incorporated by reference in their entirety.

BACKGROUND

Field of the Invention

The present disclosure relates generally to intravascular ultrasound (IVUS) imaging inside the living body and, in particular, to an IVUS imaging catheter that produces high resolution intravascular multi-frequency imaging using high bandwidth transducer outputs.

Description of Related Art

Intravascular ultrasound (IVUS) imaging is widely used in interventional cardiology as a diagnostic tool for a diseased vessel, such as an artery, within the human body to determine the need for treatment, to guide the intervention, and/or to assess its effectiveness. IVUS imaging uses ultrasound echoes to create an image of the vessel of interest. The ultrasound waves pass easily through most tissues and blood, but they are partially reflected from discontinuities arising from tissue structures (such as the various layers of the vessel wall), red blood cells, and other features of interest. The IVUS imaging system, which is connected to an IVUS catheter by way of a patient interface module (PIM), processes the received ultrasound echoes to produce a cross-sectional image of the vessel where the catheter is placed.

In order to obtain a more accurate picture of the tissue, it is desirable to use multiple ultrasound frequencies. Thus, certain portions of the tissue of interest have a better resolution at a lower frequency, and certain portions of the tissue of interest have a better resolution at a higher frequency. Current IVUS solutions providing lower frequency images and high frequency images typically present the images separately. This has the inconvenience that the viewer has to correlate two images from the same tissue area by eye. One of the images having a better quality in a certain portion of the tissue, and another image having a better quality in a different portion of the tissue.

While existing IVUS methods deliver useful diagnostic information, there is a need to combine the enhanced image quality of multiple frequencies in a single image to facilitate analysis of the tissue condition.

What is needed is a method for multi-frequency intravascular imaging to assess lesions, characterize vessels or to monitor other structures within a patient's body.

SUMMARY

The present disclosure provides a system for outputting a composite IVUS image created from two different ultrasound frequencies along with a method for forming the composite image.

According to some embodiments a method for imaging a volume within a patient volume may include generating a first signal and a second signal, directing the first signal and the second signal to a spot in the patient volume; receiving a first response signal and a second response signal from the spot in the patient volume; providing a first image from of the patient volume using the first response signal; providing a second image from the patient volume using the second response signal; and combining the first image and the second image to form a combined image.

According to some embodiments, a method for combining a plurality of images to form an image may include receiving a plurality of images collected at a plurality of frequency ranges; selecting a region of interest including the plurality of images; selecting a plurality of border lines separating the region of interest into a plurality of sub-regions; and selecting data from an image in a sub-region; forming an image in the region of interest.

These and other embodiments of the present invention will be described in further detail below with reference to the following drawings.

DETAILED DESCRIPTION

Figure 1A:
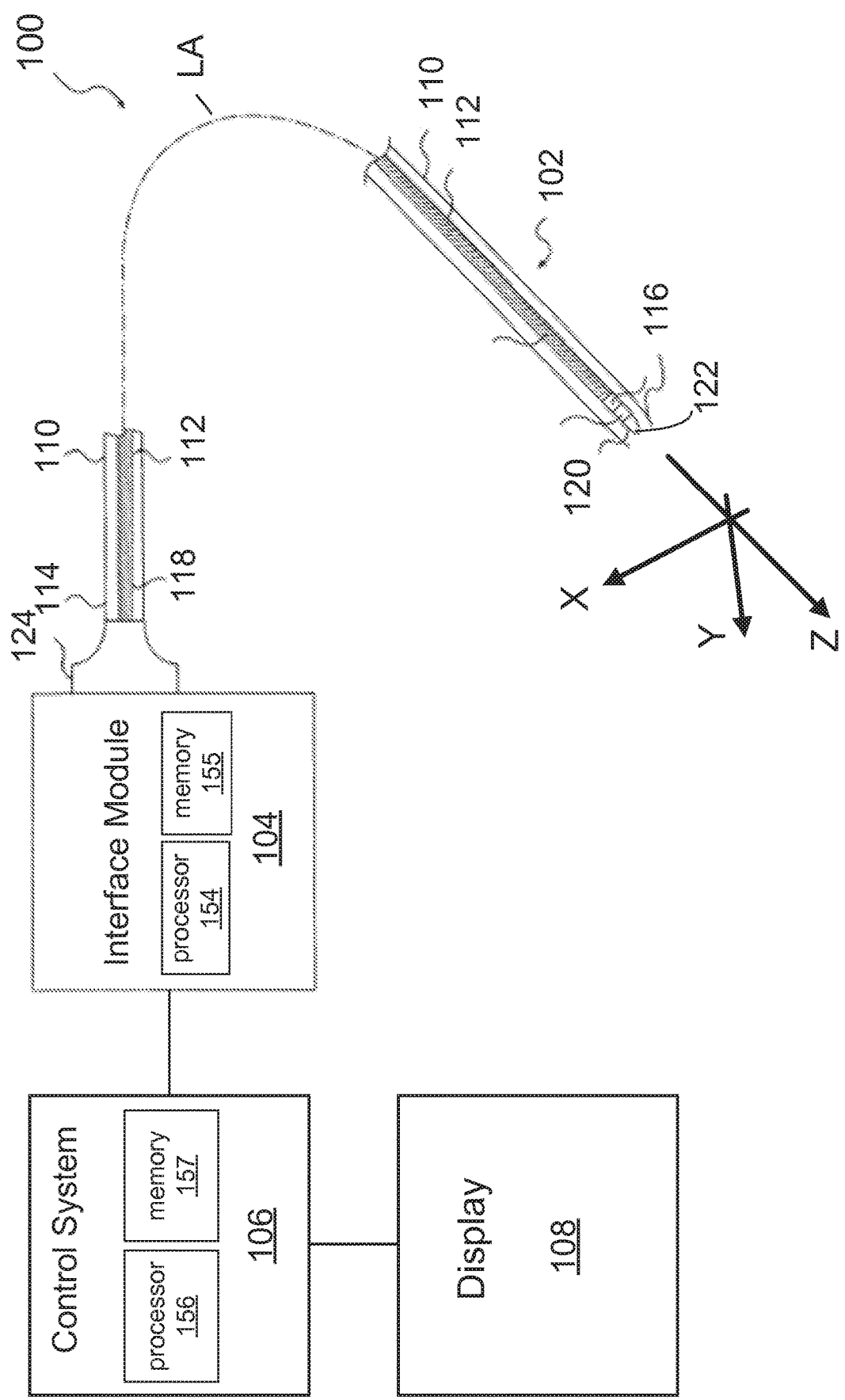
FIG. 1A is a schematic illustration of an intravascular ultrasound (IVUS) imaging system, according to some embodiments.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In embodiments of an IVUS catheter disclosed herein, an ultrasound transducer assembly is located at the tip of a flexible driveshaft that spins inside a plastic sheath inserted into the vessel of interest. The transducer assembly includes components oriented such that an ultrasound beam produced by the component propagates generally perpendicular to the axis of the catheter. A fluid-filled sheath protects the vessel tissue from the spinning transducer and driveshaft while permitting ultrasound signals to freely propagate from the transducer into the tissue and back. As the driveshaft rotates (typically at 30 revolutions per second), the transducer is periodically excited with a high voltage pulse to emit a short burst of ultrasound. The same transducer then listens for the returning echoes reflected from various tissue structures, and the IVUS imaging system assembles a two dimensional display of the vessel cross-section from a sequence of several hundred of these pulse/acquisition cycles occurring during a single revolution of the transducer.

In a rotational IVUS catheter, the ultrasound transducer may be a piezoelectric ceramic element with low electrical impedance capable of directly driving an electrical cable connecting the transducer to the imaging system hardware. In this case, a single pair of electrical leads (or coaxial cable) can be used to carry the transmit pulse from the system to the transducer and to carry the received echo signals from the transducer back to the imaging system by way of a patient interface module ("PIM") where echo signals can be assembled into an image. In embodiments where the catheter driveshaft and transducer are spinning (in order to scan a cross-section of the artery) and the imaging system hardware is stationary, an electromechanical interface couples the electrical signal to a rotating junction. In rotational IVUS imaging systems, this may be achieved by using a rotary transformer, slip rings, rotary capacitors, etc.

In some embodiments, an IVUS catheter may include a plurality of transducer components in a static configuration, forming a phased-array transducer assembly.

In addition to generating data using multiple frequencies and collecting a plurality of data-sets from a single tissue volume some embodiments assemble the multiple data sets to form a more detailed composite image of the tissue of interest. Embodiments consistent with the present disclosure include steps to combine multiple data sets to display a single image of the tissue of interest.

Reference will now be made to a particular embodiments of the concepts incorporated into an intravascular ultrasound system. However, the illustrated embodiments and uses thereof are provided as examples only. Without limitation on other systems and uses, such as but without limitation, imaging within any vessel, artery, vein, lumen, passage, tissue or organ within the body. While the following embodiments may refer to a blood vessel and a blood vessel wall for illustrative purposes, any other tissue structure may be envisioned to be imaged according to methods disclosed herein. More generally, any volume within a patient's body may be imaged according to embodiments disclosed herein, the volume including vessels, cavities, lumens, and any other tissue structures, as one of ordinary skill may recognize.

FIG. 1A is a schematic illustration of an intravascular ultrasound (IVUS) imaging system 100, according to some embodiments. IVUS imaging system 100 includes an IVUS catheter 102 coupled by a patient interface module (PIM) 104 to an IVUS control system 106. Control system 106 is coupled to a monitor 108 that displays an IVUS image (such as an image generated by IVUS system 100).

In some embodiments, catheter 102 is a rotational IVUS catheter, which may be similar to a Revolution® Rotational IVUS Imaging Catheter available from Volcano Corporation and/or rotational IVUS catheters disclosed in U.S. Pat. Nos. 5,243,988 and 5,546,948, both of which are incorporated herein by reference in their entirety, for all purposes. In some embodiments, catheter 102 may be a stationary component.

Catheter 102 includes an elongated, flexible catheter sheath 110 (having a proximal end portion 114 and a distal end portion 116) shaped and configured for insertion into a lumen of a blood vessel (not shown). In some embodiments, IVUS system 100 may be used for neurological evaluations in blood vessels in the brain, and for renal denervation in blood vessels in the kidney. A longitudinal axis LA of catheter 102 extends between the proximal end portion 114 and the distal end portion 116. Catheter 102 is flexible such that it can adapt to the curvature of the blood vessel during use. In that regard, the curved configuration illustrated in FIG. 1A is for exemplary purposes and in no way limits the manner in which catheter 102 may curve in other embodiments. Generally, catheter 102 may be configured to take on any desired straight or arcuate profile when in use.

In some embodiments an imaging core 112 extends within sheath 110. Accordingly, in some embodiments imaging core 112 may be rotated while sheath 110 remains stationary. Imaging core 112 has a proximal end portion 118 disposed within the proximal end portion 114 of sheath 110 and a distal end portion 120 disposed within the distal end portion 116 of sheath 110. The distal end portion 116 of sheath 110 and the distal end portion 120 of imaging core 112 are inserted into the vessel of interest during operation of the IVUS imaging system 100. The usable length of catheter 102 (for example, the portion that can be inserted into a patient, specifically the vessel of interest) can be any suitable length and can be varied depending upon the application. Proximal end portion 114 of sheath 110 and proximal end portion 118 of imaging core 112 are connected to PIM 104. Proximal end portions 114, 118 are fitted with a catheter hub 124 that is removably connected to PIM 104. Catheter hub 124 facilitates and supports a rotational interface that provides electrical and mechanical coupling between catheter 102 and PIM 104.

Distal end portion 120 of imaging core 112 includes a transducer assembly 122. In some embodiments, transducer assembly 122 is configured to be rotated (either by use of a motor or other rotary device, or manually by hand) to obtain images of the vessel. Transducer assembly 122 can be of any suitable type for visualizing a vessel and, in particular, a stenosis in a vessel. In the depicted embodiment, transducer assembly 122 includes a piezoelectric micro-machined ultrasonic transducer ("PMUT") and associated circuitry, such as an application-specific integrated circuit (ASIC). An exemplary PMUT used in IVUS catheters may include a polymer piezoelectric membrane, such as that disclosed in U.S. Pat. No. 6,641,540, U.S. Patent Application No. 2014/0180117, U.S. Pat. Nos. 9,345,459 and 9,717,475, each hereby incorporated by reference in its entirety. The PMUT may provide greater than 100% bandwidth for optimum resolution in a radial direction, and a spherically-focused aperture for optimum azimuthal and elevation resolution. Thus, transducer assembly 122 may provide a focused ultrasonic beam having a spot size of about 50 μm or less.

In some embodiments transducer assembly 122 may include a plurality of stationary components disposed around the circumference of distal end 120 of catheter 102. In such configuration, the components in transducer 122 may be piezo-electric elements distributed to form a phased-array configuration. The piezo-electric elements may be ceramic-based or polymer-based. Furthermore, in some embodiments the plurality of stationary components in transducer 122 may be configured to produce a focused acoustic impulse. In such embodiments, the stationary components produce an acoustic impulse according to a pre-selected excitation phase for each of the components.

Transducer assembly 122 may also include a housing having the PMUT and associated circuitry disposed therein. In some embodiments the housing has an opening that ultrasound signals generated by the PMUT transducer travel through. Alternatively, transducer assembly 122 includes a capacitive micro-machined ultrasonic transducer ("CMUT"). In yet another alternative embodiment, the transducer assembly 122 includes an ultrasound transducer array (for example, arrays having 16, 32, 64, or 128 components are utilized in some embodiments).

In some embodiments, a rotation of imaging core 112 within sheath 110 is controlled by PIM 104. For example, PIM 104 provides user interface controls that can be manipulated by a user. In some embodiments PIM 104 may receive, analyze, and/or display information received through imaging core 112. It will be appreciated that any suitable functionality, controls, information processing and analysis, and display can be incorporated into PIM 104. Thus, PIM 104 may include a processor circuit 154 and a memory circuit 155 to execute operations on catheter 102 and receive, process, and store data from catheter 102. In some embodiments PIM 104 receives data associated to ultrasound signals (echoes) detected by imaging core 112. PIM 104 processes the data and forwards the processed echo data to control system 106. Control system 106 may include a processor circuit 156 and a memory circuit 157 to execute operations on catheter 102 and receive, process, and store data from catheter 102. In some embodiments, PIM 104 performs preliminary processing of the echo data prior to transmitting the echo data to control system 106. PIM 104 may perform amplification, filtering, and/or aggregating of the echo data, using processor circuit 154 and memory circuit 155. PIM 104 can also supply high- and low-voltage DC power to support operation of catheter 102 including circuitry within transducer assembly 122.

In some embodiments, wires associated with IVUS imaging system 100 extend from control system 106 to PIM 104. Thus, signals from control system 106 can be communicated to PIM 104 and/or vice versa. In some embodiments, control system 106 communicates wirelessly with PIM 104. Similarly, it is understood that, in some embodiments, wires associated with IVUS imaging system 100 extend from control system 106 to monitor 108 such that signals from control system 106 can be communicated to monitor 108 and/or vice versa. In some embodiments, control system 106 communicates wirelessly with monitor 108.

Piezoelectric micro-machined ultrasound transducers (PMUTs) fabricated using a polymer piezoelectric material for use in transducer assembly 122, such as disclosed in U.S. Pat. No. 6,641,540 that is hereby incorporated by reference in its entirety, offer greater than 100% bandwidth for optimum resolution in the radial direction, and a spherically-focused aperture for optimum azimuthal and elevation resolution.

FIG. 1A illustrates a 3-dimensional (3D) Cartesian coordinate system XYZ oriented such that the Z-axis is aligned with the LA. In further descriptions of embodiments disclosed herein, a reference to a Cartesian plane or coordinate may be made in relation to FIG. 1. One of ordinary skill will recognize that the particular choice of coordinate axes in FIG. 1A is not limiting of embodiments as disclosed herein. The choice of coordinate axes is done for illustration purposes only.

Figure 1B:
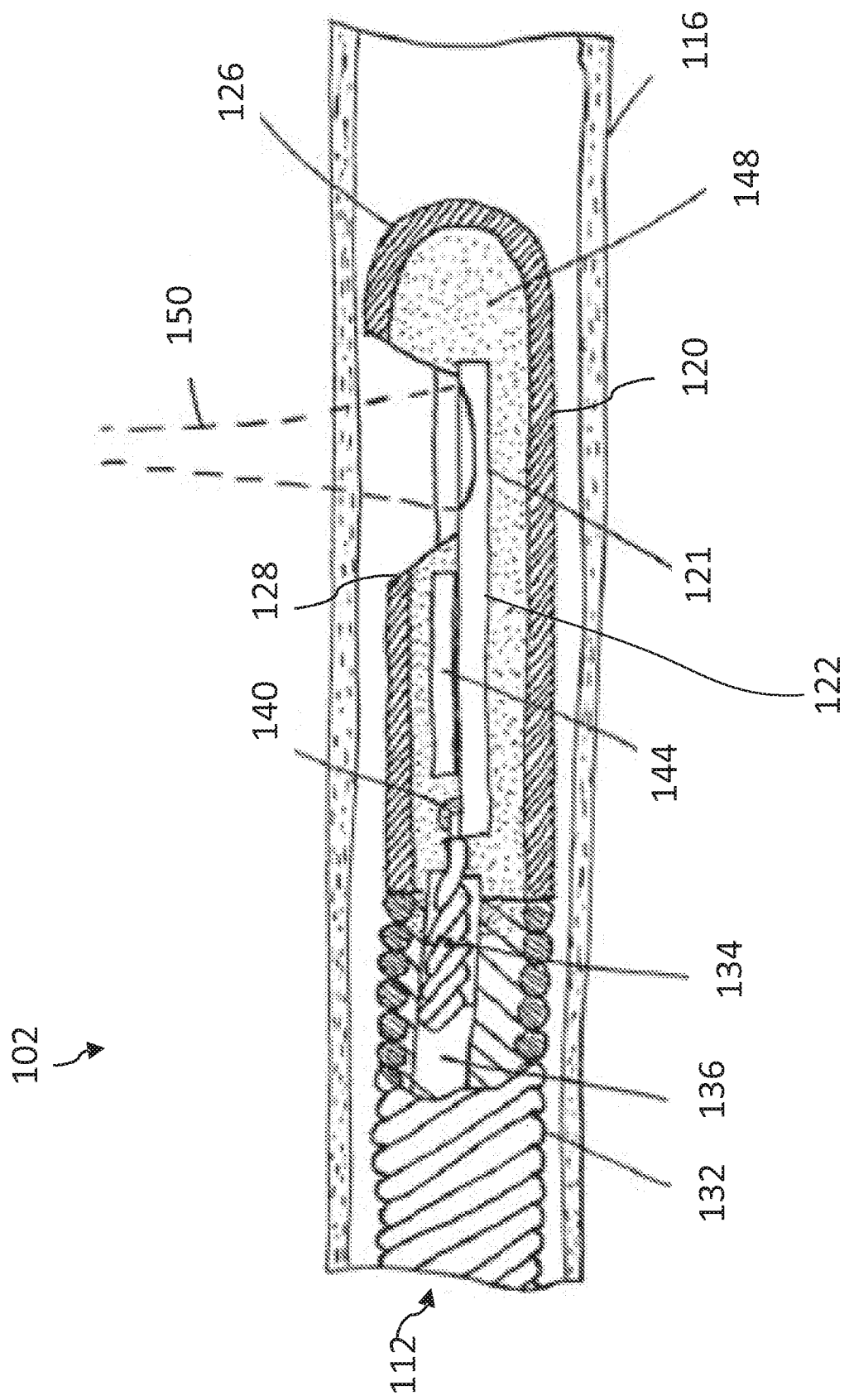
FIG. 1B is a cross-sectional side view of a distal portion of a catheter used in an IVUS imaging system, according to some embodiments.

FIG. 1B is a cross-sectional side view of a distal portion of a catheter used in an IVUS imaging system, according to some embodiments. In particular, FIG. 1B shows an expanded view of aspects of the distal portion of imaging core 112. In this exemplary embodiment, imaging core 112 is terminated at its distal tip by a housing 126 having a rounded nose and a cutout 128 for the ultrasound beam 150 to emerge from the housing. In some embodiments, a flexible driveshaft 132 of imaging core 112 is composed of two or more layers of counter wound stainless steel wires, welded, or otherwise secured to housing 126 such that rotation of the flexible driveshaft also imparts rotation to housing 126. In the illustrated embodiment, a PMUT MEMS transducer layer 121 includes a spherically focused portion facing cutout 128. In some embodiments, transducer assembly 122 may include application-specific integrated circuit (ASIC) 144 within distal portion 120 of imaging core 112. ASIC 144 is electrically coupled to transducer layer 221 through two or more connections.

In some embodiments of the present disclosure ASIC 144 may include an amplifier, a transmitter, and a protection circuit associated with PMUT MEMS layer 121. In some embodiments, ASIC 144 is flip-chip mounted to a substrate of the PMUT MEMS layer 121 using anisotropic conductive adhesive or suitable alternative chip-to-chip bonding method. When assembled together PMUT MEMS layer 121 and ASIC 144 form an ASIC/MEMS hybrid transducer assembly 122 mounted within housing 126. An electrical cable 134 with optional shield 136 may be attached to transducer assembly 122 with solder 140. Electrical cable 134 may extend through an inner lumen of the flexible driveshaft 132 to proximal end 118 of imaging core 112. In proximal end 118, cable 134 is terminated to an electrical connector portion of a rotational interface coupling catheter 102 to PIM 104 (cf. FIG. 1A). In the illustrated embodiment, transducer assembly 122 is secured in place relative to the housing 126 by an epoxy 148 or other bonding agent. Epoxy 148 may serve as an acoustic backing material to absorb acoustic reverberations propagating within housing 126 and as a strain relief for the electrical cable 134 where it is soldered to transducer assembly 122.

Figure 2:
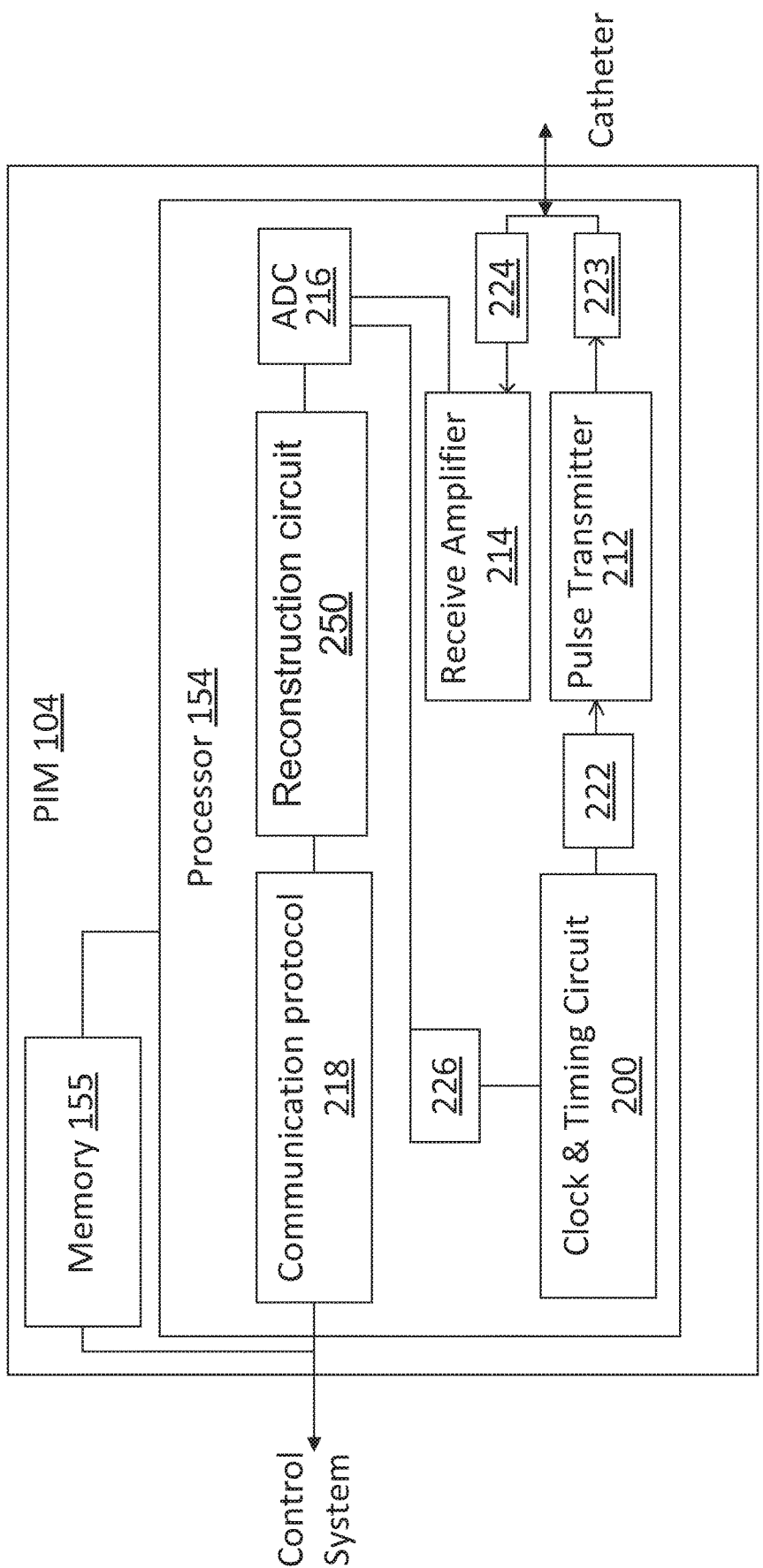
FIG. 2 is a block diagram of a Patient Interface Module (PIM) for use in an IVUS imaging system, according to some embodiments.

FIG. 2 is a block diagram of a Patient Interface Module (PIM) 104 for use in an IVUS imaging system, according to some embodiments. PIM 104 includes processor circuit 154 and memory circuit 155, described in detail above in relation to FIG. 1. PIM 104 provides a control signal 223 to a catheter, and receives data 224 from the catheter (e.g., catheter 102, FIG. 1). Control signal 223 may include a sequence of voltage pulses creating an acoustic impulse from a transducer assembly (e.g., transducer assembly 122). In some embodiments, control signal 223 is generated in a pulse transmitter 212 included in processor circuit 154. In some embodiments, each pulse from a plurality of pulses may include a single cycle of a signal having a selected frequency. In such embodiments, the frequency spectrum of such a pulse will be a signal centered at the selected frequency, having a bandwidth. Accordingly, pulse transmitter 212 may be configured to generate a plurality of voltage pulses centered at a plurality of frequencies. For example, the plurality of center frequencies for pulses provided by pulse transmitter 212 may include different frequencies, such as baseband frequencies and their harmonics. Thus, according to some embodiments, pulse transmitter circuit 212 has a transmission band which may include multiple center frequencies for a plurality of pulses provided to a transducer assembly.

In some embodiments, data 224 includes electrical signals received from catheter 102 and amplified by receive amplifier 214. The electrical signals in data 224 may be voltage signals. According to some embodiments, data 224 is an analog signal associated to an ultrasonic echo from a tissue structure around the transducer assembly. Analog-to-digital converter (ADC) 216 converts amplified electrical signal 224 into a digital signal. In some embodiments, the digital signal from ADC 216 is further processed by a reconstruction circuit 250. In some embodiments, data 224 includes voltage signals produced by the transducer assembly upon receiving an ultrasound echo signal from a tissue structure. The tissue structure may be surrounding a distal end of a catheter that includes the transducer assembly (e.g., distal end 120, cf. FIG. 1). The voltage signal in data 224 may include tissue responses at a plurality of frequencies, forming a reception band. Thus, receive amplifier 214 may include filters that produce a bandwidth including the reception band. Accordingly, in some embodiments the filtering of incoming data 224 and outgoing control signal 223 may be performed by ASIC 144 at distal end portion 120 of catheter 102 (cf. FIG. 1B).

Reconstruction circuit 250 may perform operations on the digitized, amplified data 224 such as data smoothing, averaging, noise filtering, and data interpolation. Thus, in some embodiments reconstruction circuit 250 may prepare the data provided by transducer assembly 122 for an image rendition of the tissue surrounding distal end 120 of catheter 102. The reconstructed digital data is transferred out of PIM 104 to IVUS control system 106 by a communication protocol circuit 218.

In some embodiments, a clock and timing circuit 200 provides a digitizing signal 226 to ADC 216, and transmitter timing signal 222 to pulse transmitter 212. According to some embodiments, clock and timing circuit 200 provides transmitter timing signal 222 and digitizing signal 226 using a common stable system clock. Some embodiments may include a phase-locked loop circuit in clock and timing circuit 200 to synchronize transmitter timing signal 222 and digitizing signal 226. In some embodiments transmitter timing signal 222 and digitizing signal 226 have the same phase, or their relative phase is fixed in time to within the resolution of clock and timing circuit 200.

Figure 3A:
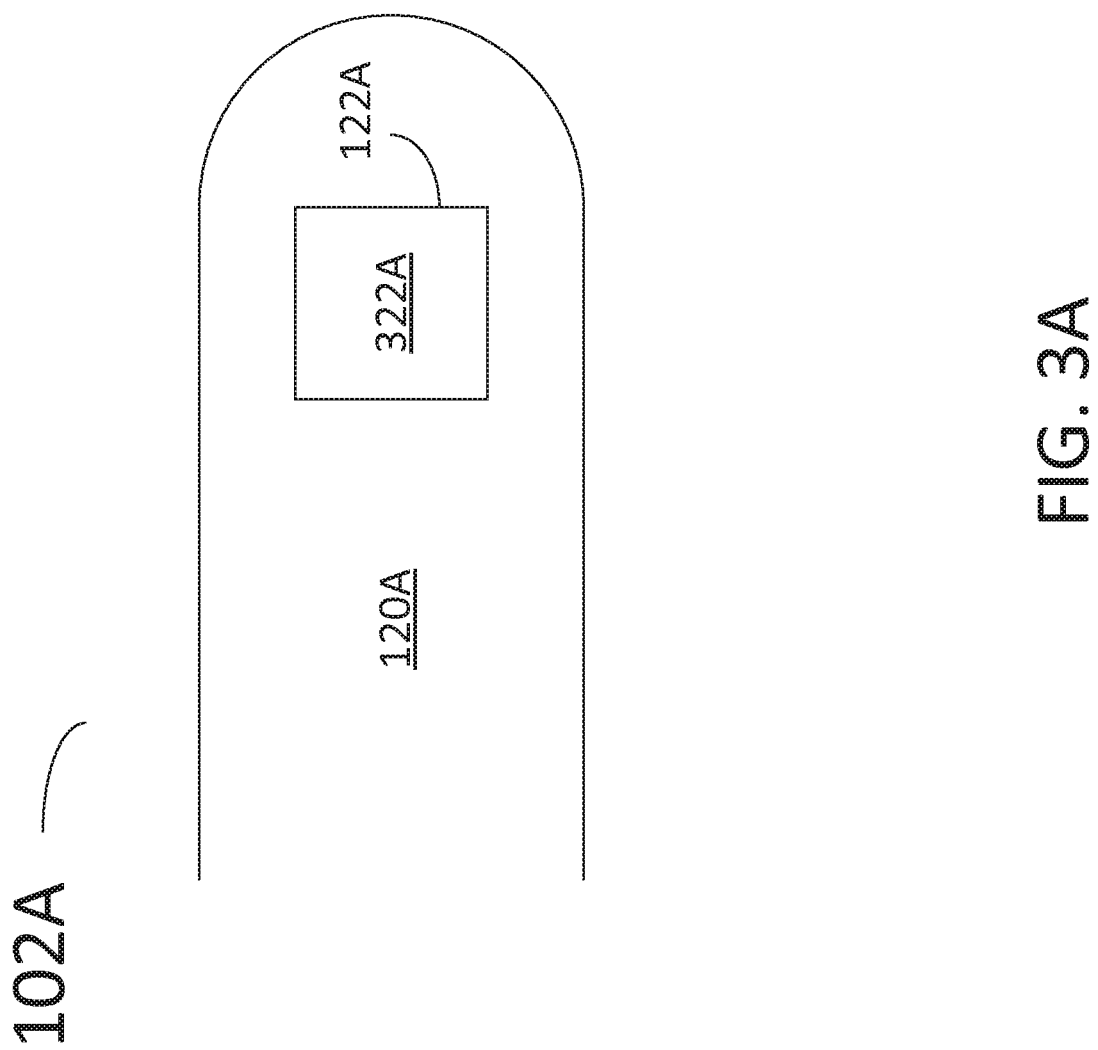
FIG. 3A is a partial illustration of a distal end of a catheter for multi-frequency imaging, according to some embodiments.

FIG. 3A is a partial illustration of a distal end 120A of a catheter 102A for multi-frequency imaging, according to some embodiments. Distal end 120A includes transducer assembly 122A. Accordingly, transducer assembly 122A includes a single piezo-electric component 322A. In embodiments consistent with the present disclosure, piezo-electric component 322A may have a response band that includes the transmission band of a pulse transmitter 212 and the reception band of receive amplifier 214. The response band of piezo-electric component 322A is determined by the material forming the component, and the geometry of the component. According to some embodiments, the response band of a transducer element is measured by the voltage amplitude produced when an acoustic wave of a certain frequency impinges on the transducer. In some embodiments, it is desirable to have a broad response bandwidth for piezo-electric component 322A. For example, in some embodiments a response band from about 5 MHz to about 135 MHz may be achievable using polymer-based transducer assemblies. In some embodiments, the polymer used in transducer assembly 322A may be a ferroelectric polymer such as polyvinylidene fluoride (PVDF). Further according to some embodiments, a polymer used in transducer assembly 322A may include PVDF-co-trifluoroethylene (PVDF-TrFE) as a piezo-electric material. Alternatively, polymers such as PVDF-CTFE or PVDF-CFE may be used.

Thus, according to embodiments consistent with the present disclosure a pulse transmitter circuit 212 provides a plurality of pulses within a transmission band to a single piezo-electric component 322A. Likewise, a single piezo-electric component 322A may receive an ultrasound echo within a reception band from a tissue structure. The tissue structure may be a blood vessel wall surrounding distal end 120A of catheter 102.

Figure 3B:
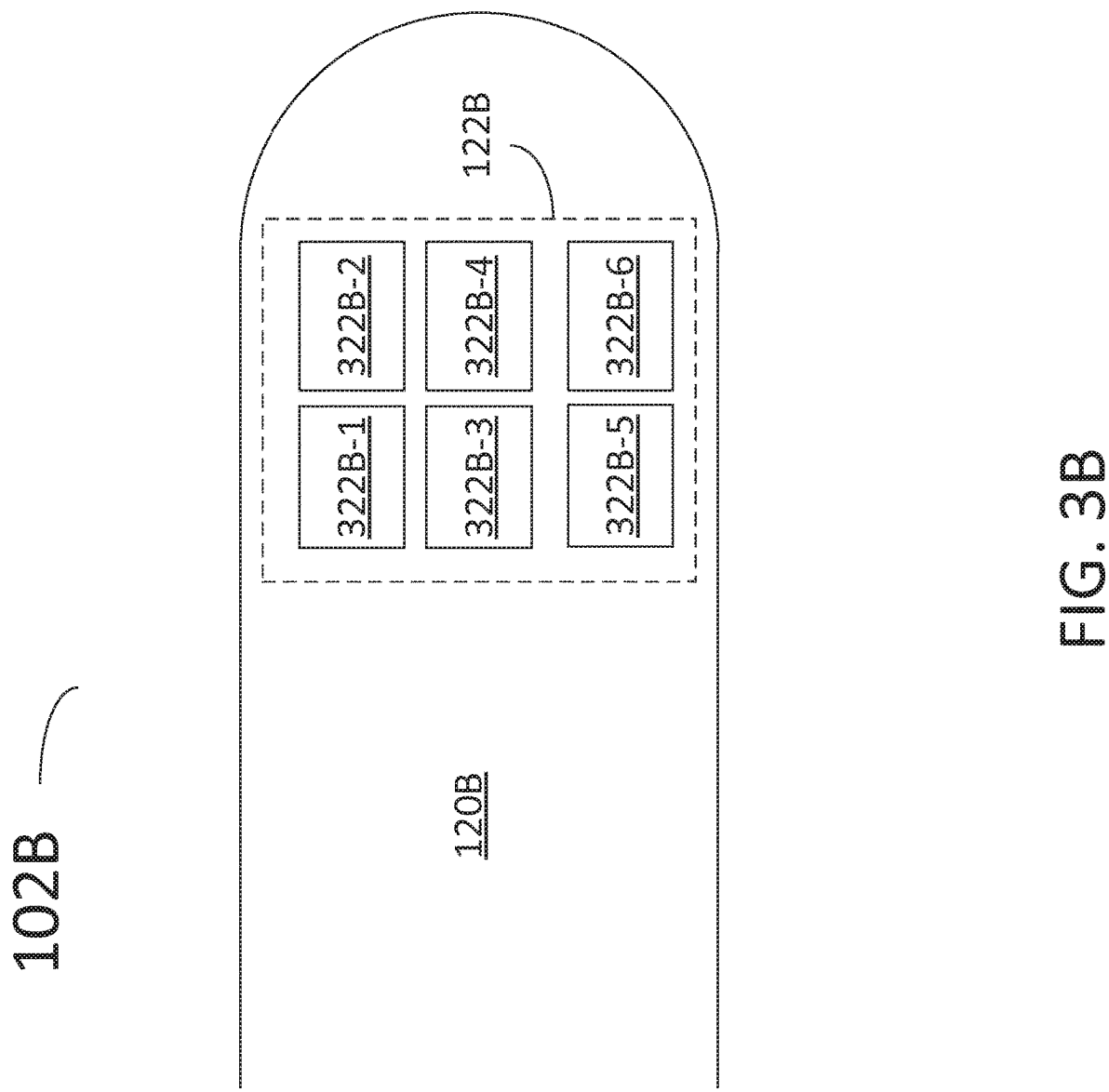
FIG. 3B is a partial illustration of a distal end of a catheter for multi-frequency imaging, according to some embodiments.

FIG. 3B is a partial illustration of a distal end 120B of a catheter 102B for multi-frequency imaging, according to some embodiments. Distal end 120B includes transducer assembly 122B. Transducer assembly 122B may include a plurality of piezo-electric components 322B-1, 322B-2, 322B-3, 322B-4, 322B-5, and 322B-6 (collectively referred to hereinafter as 'piezo-electric components 322B'). One of ordinary skill will recognize that the specific number of piezo-electric components 322B in assembly 122B is arbitrary and not limiting. Furthermore, the specific shape and arrangement of components 322B is also not limiting, depending only in the specific application of a multi-frequency imaging catheter 102.

In some embodiments, a first selected group of components 322B may be used for transmitting ultrasound pulses, and a second selected group of components 322B may be used for receiving ultrasound echoes. The first selected group of components 322B may be different from the second selected group of components 322B. Therefore, in some embodiments each of the components 322B-1 through 322B-6 may have a narrow response band, tuned to the specific function of the component (e.g., transmission, reception, or both). For example, component 322B-1 may have a response band including a portion of the transmission band. Likewise, component 322B-2 may have a response band including a portion of the reception band. Accordingly, a first selected group of ultrasound pulses provided to the first selected group of components 322B may be centered at a first selected group of frequencies. The first selected group of frequencies may include ultrasound frequencies such as 20 MHz, 40 MHz, and 80 MHz. Likewise, a receive amplifier in a processor circuit for a PIM module coupled to transducer 122B may have filters with bandwidths selected according to the response band of the second selected group of components 322B. Thus, radio-frequency (RF) filters in a response amplifier inside a PIM may be centered at a second selected group of frequencies such as 20 MHz, 40 MHz, and 80 MHz. In some embodiments, RF filters may be included in ASIC 144 at distal end portion 120 of catheter 102, to filter the echo signal in a selected response band.

Accordingly, the second selected group of frequencies may include harmonic combinations of the first selected group of frequencies. A harmonic combination may include integer multiples of a frequency in the first selected group of frequencies. In some embodiments, a harmonic combination may include a sum of frequencies from the first selected group of frequencies. For example, when a first selected group of frequencies includes 20 MHz, 40 MHz, and 80 MHz, a second selected group of frequencies may include 40 MHz (=2×20 MHz), 80 MHz (=2×40 MHz), 60 MHz (=20 MHz+40 MHz), and even 120 MHz (=40 MHz+80 MHz).

Thus, according to some embodiments, transducer assembly 122B may provide a wide response band by using multiple transducer components 322B. Each of transducer components 322B may have a narrow response band covering a portion of a transmission band or a portion of a reception band, centered at a selected frequency. Such a configuration may be desirable since piezo-electric components with a narrow response band may provide high response efficiency.

Figure 4:
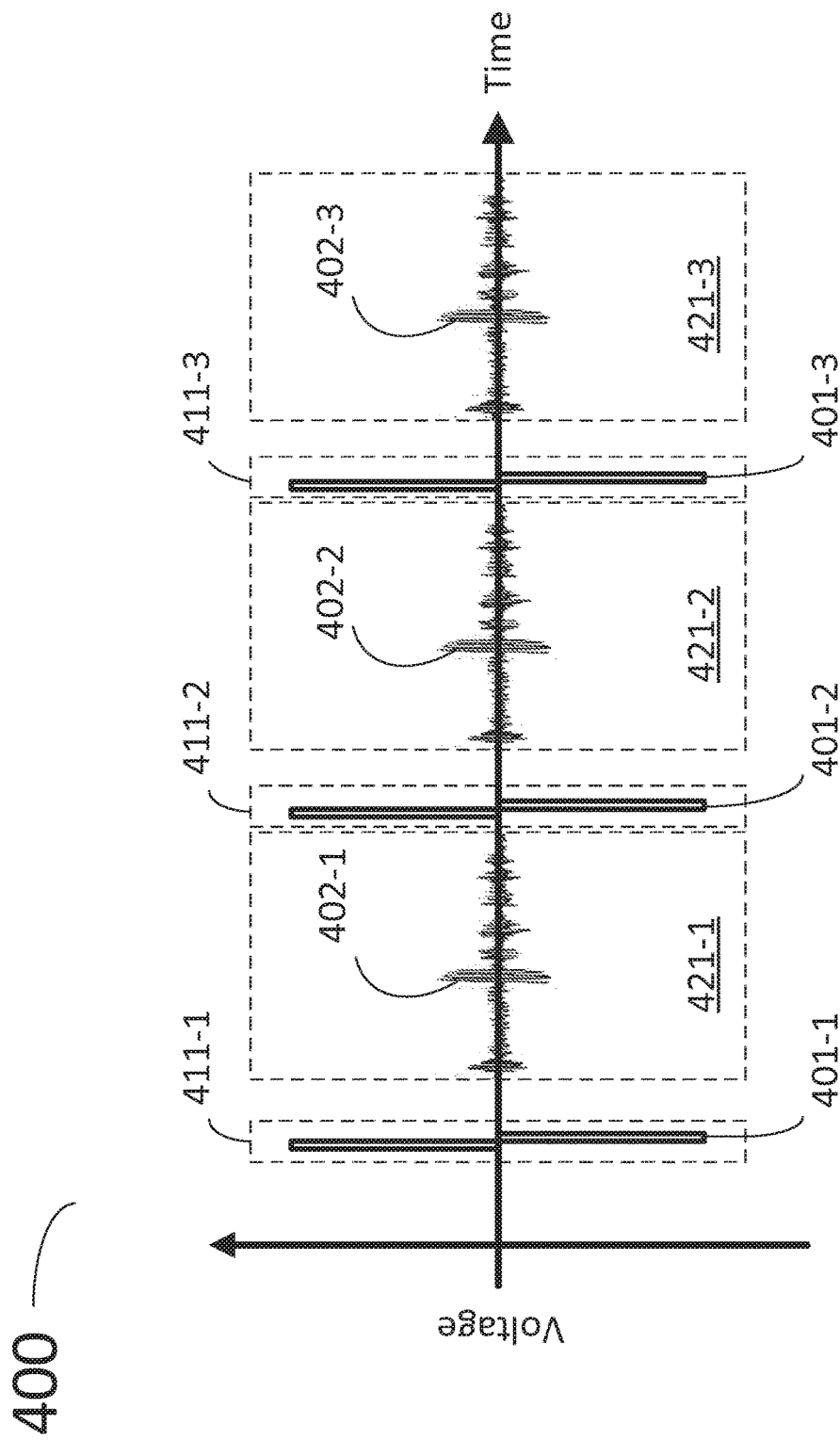
FIG. 4 is a partial schematic illustration of a transducer voltage, according to some embodiments.

FIG. 4 is a partial schematic illustration of a transducer voltage 400, according to some embodiments. Transducer voltage 400 includes voltage values across a transducer component in a transducer assembly, as a function of time (e.g., transducer assemblies 122A, 122B in FIGS. 3A, 3B above). Transducer voltage 400 includes ultrasound pulse transmit portions 411-1, 411-2, and 411-3, collectively referred to hereinafter as 'transmission portions 411.' Likewise, transducer voltage 400 includes ultrasound echo reception portions 421-1, 421-2, and 421-3, collectively referred to hereinafter as 'reception portions 421.' While FIG. 4 illustrates three transmission portions 411 and three reception portions 421, one of ordinary skill will recognize that there is nothing limiting in the number of transmission portions 411, and reception portions 421 that may be used. Moreover, in some embodiments the number of transmission portions 411 may be different from the number of reception portions 421. FIG. 4 illustrates each one of transmission portions 411 followed by a reception portion 421. It will be recognized by those with ordinary skill that one or more transmission portions 411 may be provided in sequence, before a reception portion 421 follows. Likewise, a plurality of reception portions 421 may be provided in sequence, after a transmission portion 411.

Transmission portions 411 include pulses 401-1, 401-2, and 401-3 provided by a pulse transmitter circuit (e.g., pulse transmitter 212, cf. FIG. 2) to the transducer assembly. Pulses 401-1 through 401-3 are collectively referred to hereinafter as pulses 401. Reception portions 421 include signals 402-1, 402-2, and 402-3 provided by the transducer assembly to an amplifier circuit (e.g., receive amplifier 214, cf. FIG. 2). Signals 402-1, 402-2, and 402-3 are referred to hereinafter as ultrasound echo signals 402. Accordingly, ultrasound echo signals 402 may be tissue responses to pulses 401. Moreover, depending on the frequency component of pulses 401, ultrasound echo signals 402 may proceed from different portions of a tissue structure surrounding the transducer assembly. Thus, ultrasound echo signal 402-3 corresponding to a pulse 401-3 having a high center frequency may proceed from a shallow region of the tissue structure. For example, a signal 402 corresponding to a pulse 401 centered at about 80 MHz may proceed from an area of a blood vessel wall proximate to the lumen of the vessel.

Figure 5:
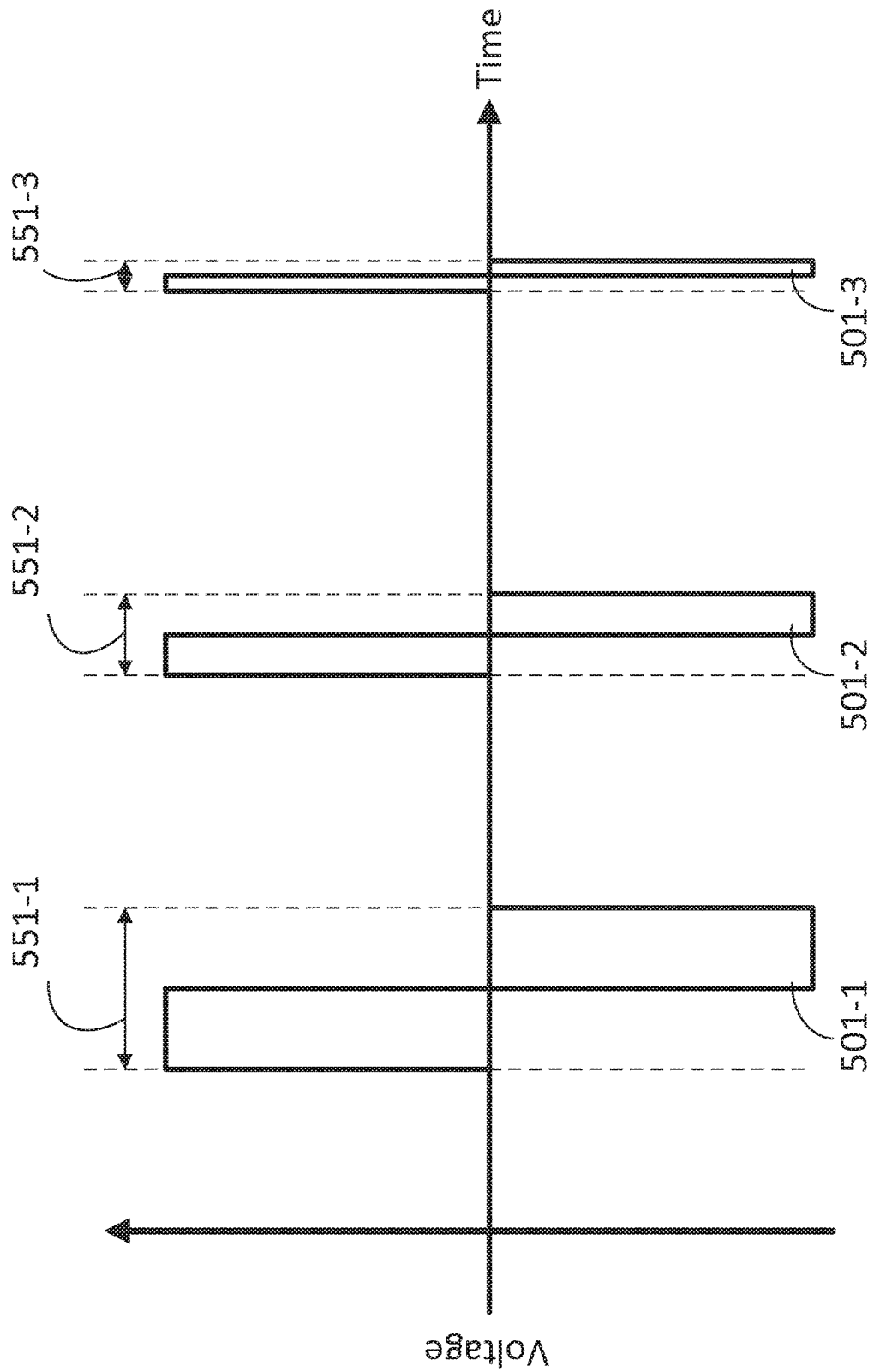
FIG. 5 is a partial schematic illustration of multi-frequency voltage pulses for a transducer component, according to some embodiments.

FIG. 5 is a partial schematic illustration of multi-frequency voltage pulses for a transducer component, according to some embodiments. FIG. 5 illustrates voltage pulses 501-1, 501-2, and 501-3, collectively referred hereinafter as voltage pulses 501. Consistent with FIG. 5, each of pulses 501 includes a cycle having a period 551-1, 551-2, and 551-3, collectively referred hereinafter as period values 551. Accordingly, period 551-1 may be different from period 551-2, thus corresponding to a pulse 501-1 centered at a lower frequency than the center frequency of pulse 501-2. For example, if period 551-1 is double the length of period 551-2, the center frequency of pulse 501-2 will be at double the frequency of the center of pulse 501-1. Likewise, period 551-3 may be even shorter than period 551-1, corresponding to an even higher center frequency for pulse 501-3. One of ordinary skill will recognize that pulses 501 may include any one of a plurality of period values 551.

In embodiments consistent with the present disclosure it is desirable that the transducer assembly receiving pulses 501 has a response bandwidth including the center frequencies of each of pulses 501. In some embodiments using a plurality of transducer components (e.g., components 322B, FIG. 3B), each of pulses 501 may be directed to a different transducer component optimized to operate at a specific center frequency. For example, transducer component 322B-1 may be designed to operate with maximum efficiency at the center frequency corresponding to period 551-1. One of ordinary skill will recognize that there is no limitation as to the number of different periods 551 that may be provided. Also, the specific center frequency associated to a given period 551 may be chosen according to a specific application or need. For example, a period 551 may correspond to a frequency of 20 MHz, 40 MHz, 80 MHz, or more. In some embodiments, one of periods 551 may include a frequency of 10 MHz, or less.

In addition to obtaining information from different portions of a tissue structure using multi-frequency pulses as in FIG. 5, images having different axial resolution may be obtained. For example, an image generated with ultrasound echo signal from pulse 501-1 may have longer penetration depth within the tissue, and lower axial resolution, compared to an image generated from pulse 501-2. An image obtained from pulse 501-3 may provide higher axial resolution at a lower penetration depth.

Figure 6:
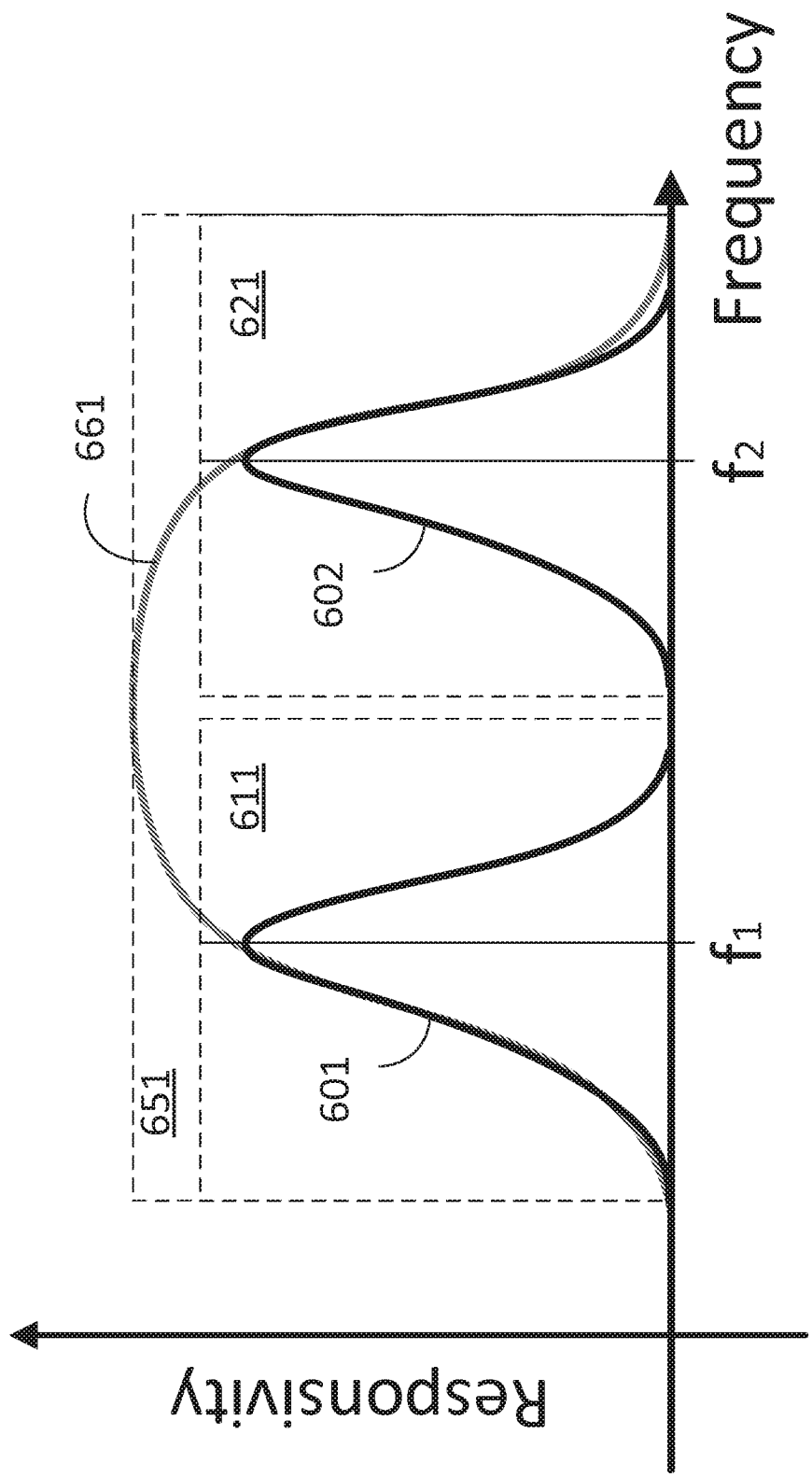
FIG. 6 is a partial schematic illustration of a transmission band, a reception band, and a response band in a multi-frequency IVUS imaging system, according to some embodiments.

FIG. 6 is a partial schematic illustration of a transmission band 611, a reception band 621, and a response band 651 in a multi-frequency IVUS imaging system, according to some embodiments. In FIG. 6, response band 651 is a broad band including transmission band 611 and reception band 621. Transmission band 611 includes a transmission curve 601 centered at a first frequency f1, and reception band 621 includes a reception curve 602 centered at a second frequency, f2. According to some embodiments, the second frequency may be a second harmonic of the first frequency (f2=2×f1). An embodiment such as illustrated in FIG. 6 may correspond to the spectral configuration of a multi-frequency IVUS imaging system using a single transducer (e.g., transducer 122A, cf. FIG. 3A). In some embodiments reception band 621 may lay outside of response band 651 of the transducer providing transmission band 611. Such embodiments may correspond to a multi-frequency IVUS imaging system using a plurality of transducer components (e.g., transducer 122B, FIG. 3B). For example, transmission band 611 and response band 661 may correspond to transducer component 322B-1. Further, reception band 621 from component 322B-2 may be outside of response band 661.

A multi-frequency IVUS imaging system as disclosed herein may include a PIM coupled to a catheter having a transducer assembly with a transmission band, a reception band, and a response band as illustrated in FIG. 6 (e.g., system 100, PIM 104, catheter 102, and transducer assembly 122, FIG. 1). The PIM may include a processor circuit to provide a pulse signal to the transducer assembly and receive an ultrasound echo from the signal (e.g., processor circuit 154). The processor circuit may include a pulse transmitter circuit having a bandwidth such as transmission band 611 (e.g., pulse transmitter 212). The processor circuit may also include a receive amplifier having a bandwidth as reception band 621 (e.g., receive amplifier 214). The bandwidth of the pulse transmission circuit and the receive amplifier circuit may be adjusted using RF circuit filtering techniques. In some embodiments RF circuit filters may be included in ASIC 144, at distal end portion 120 of catheter 102.

Figure 7:
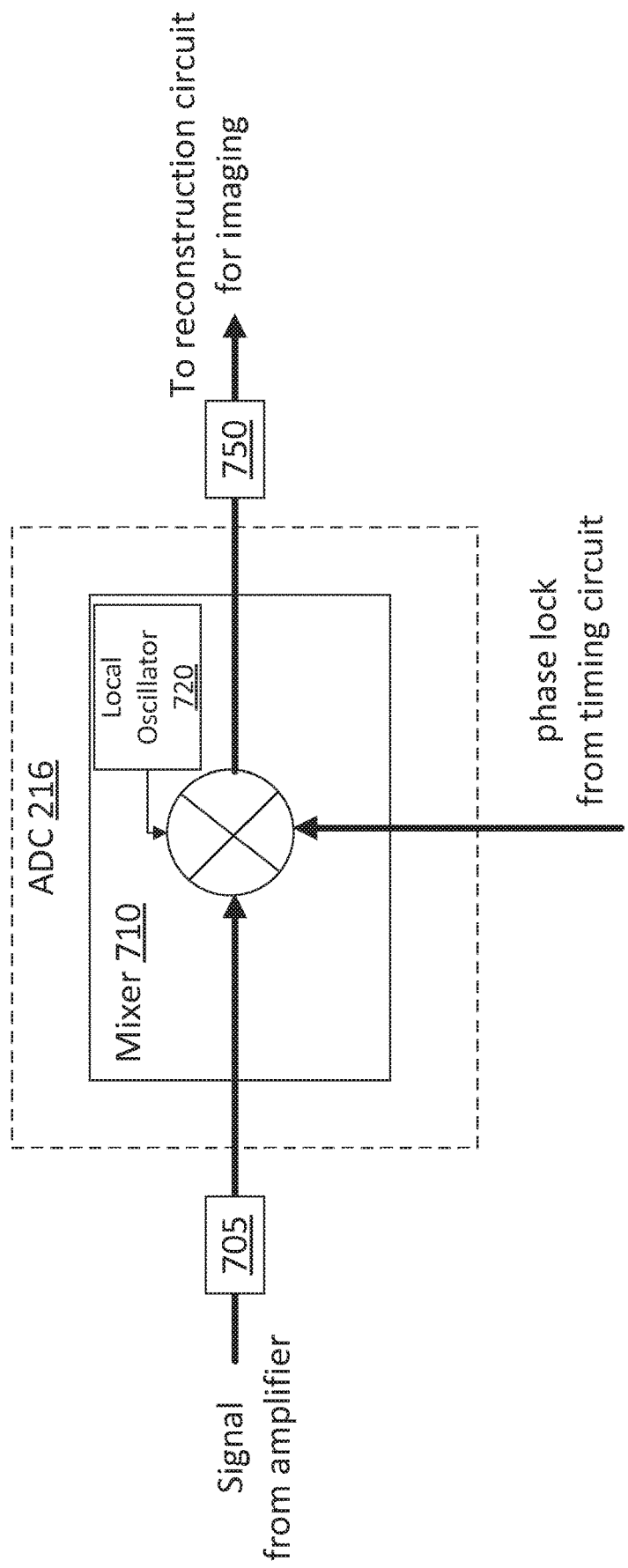
FIG. 7 is a partial schematic illustration of a signal processing strategy for selecting harmonic components of a signal, according to some embodiments.

FIG. 7 is a partial schematic illustration of a signal processing strategy for selecting harmonic components 750 of a signal 705, according to some embodiments. In some embodiments, an ADC circuit includes a frequency mixer 710 (e.g., ADC 216, FIG. 2). Mixer 710 combines signal 705 from an amplifier circuit with a local oscillator signal at a harmonic frequency 720. In some embodiments, the harmonic frequency of the local oscillator is an integer multiple of a center frequency included in a pulse signal for a transducer assembly (e.g., any one of pulses 501, cf. FIG. 5). For example, if a center frequency in a pulse signal is the harmonic frequency 720 of the local oscillator in mixer 710 may be '2×f'. Frequency mixer 710 may include a feedback circuit using a phase-lock signal provided by a timing circuit (e.g., clock and timing circuit 200, FIG. 2). For example, in some embodiments the phase lock signal may be included in digitizing signal 226 (cf. FIG. 2). Harmonic component 750 of signal 705 may thus be transmitted to a reconstruction circuit for imaging (e.g., reconstruction circuit 250).

Figure 8:
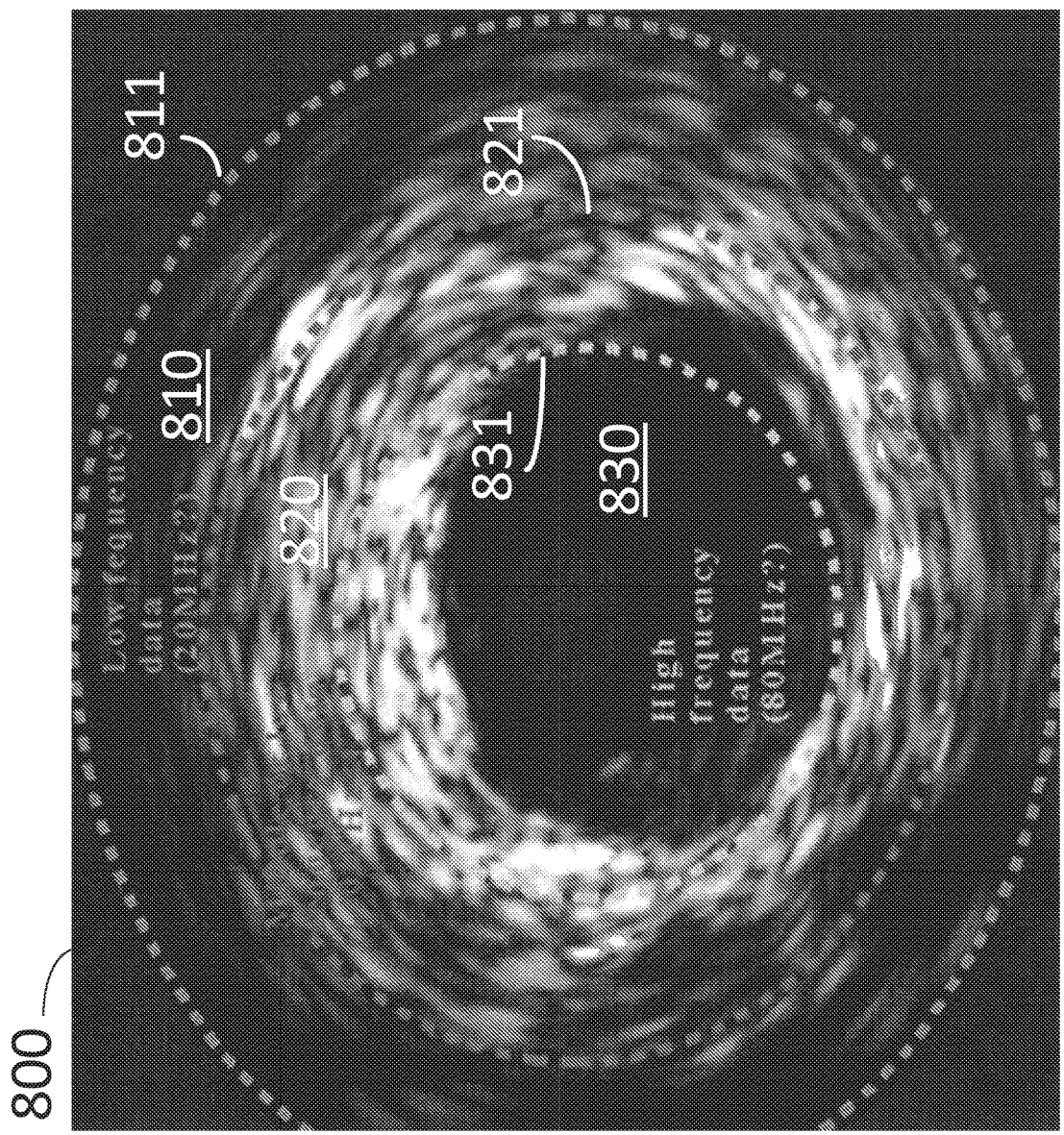
FIG. 8 is a schematic illustration of a combination of data from various frequencies displayed in an image, according to some embodiments.

FIG. 8 is a schematic illustration of a combination of data from various frequencies displayed in a composite image 800, according to some embodiments. Accordingly, FIG. 8 combines a data portion 810 obtained at a first frequency range 810, a data portion 820 obtained at a second frequency range 820, and a data portion 830 obtained at a third frequency range. According to some embodiments the first frequency range includes frequencies lower than the second frequency range. And the second frequency range includes frequencies lower than the third frequency range. For example, in some embodiments the first frequency range may include ultrasound echo signals at approximately 20 MHz, or lower. In some embodiments, the second frequency range may include ultrasound echo signals at approximately 40 MHz. And the third frequency range may include ultrasound echo signals at approximately 80 MHz, or even higher. Accordingly, data portion 810 includes data having better resolution in deeper tissue regions, as illustrated in FIG. 8. Thus, according to methods described herein, data portion 810 may be selected from an IVUS scan collected at the first frequency range. Moreover, data overlapping data portion 810 collected from an IVUS scan corresponding to either the second frequency range or the third frequency range may be discarded, since the spatial resolution in a deep tissue region may not be adequate at frequencies higher than the first frequency range.

Likewise, data portion 820 includes data having better resolution in middle tissue regions, as illustrated in FIG. 8. Thus, according to some methods described herein, data portion 820 may be selected from an IVUS scan collected at the second frequency range. Moreover, data overlapping data portion 820 collected from an IVUS scan corresponding to either the first frequency range or the third frequency range may be discarded, since the spatial resolution in a middle tissue region may not be adequate at frequencies higher and lower than the second frequency range.

Likewise, data portion 830 includes data having better resolution in shallow tissue regions, as illustrated in FIG. 8. Thus, according to some methods described herein, data portion 830 may be selected from an IVUS scan collected at the third frequency range. For example, in some embodiments where the third frequency range includes high enough frequencies, data portion 830 may include a portion of the lumen in the blood vessel, including blood. Moreover, data overlapping data portion 830 collected from an IVUS scan corresponding to either the first frequency range or the second frequency range may be discarded, since the spatial resolution in a shallow tissue region may not be adequate at frequencies lower than the third frequency range.

According to some embodiments, data portion 810 is defined by border lines 811 and 821. Likewise, data portion 820 may be defined by border lines 821 and 831. The precise location of border lines 811, 821, and 831 may be determined by knowledge of the depth of focus of the focused acoustic beam at each of the first frequency range (data portion 810), the second frequency range (data portion 820), and the third frequency range (data portion 830).

In some embodiments, a method for imaging a volume within a patient volume and producing a composite image as in FIG. 8 may include generating a first signal and a second signal, directing the first signal and the second signal to a spot in the patient volume; receiving a first response signal and a second response signal from the spot in the patient volume; providing a first image from of the patient volume using the first response signal; providing a second image from the patient volume using the second response signal; and combining the first image and the second image to form a combined image. Wherein the first image and the second image may be an image generated from any one of the first, second, and third frequency ranges described in detail above. Furthermore, as illustrated in FIG. 8, the method for imaging may include combining a first image, a second image, and a third image. One of ordinary skill in the art will recognize that any number of images may be combined in methods consistent with the present disclosure.

According to some embodiments, a method to obtain a combined image as in FIG. 8 includes selecting a common boundary in the first image and the second image (e.g., boundary 811, 821, and/or 831); selecting a first data portion from the first image on a first side of the boundary; selecting a second data portion from the second image on a second side of the boundary; and forming the combined image with the first data portion and the second data portion.

In some embodiments, selecting a common boundary includes forming a first boundary separating high quality data in the first image and a second boundary separating high quality data in the second image; and forming the common boundary selecting points close to the first boundary and the second boundary. In some embodiments, separating high quality data includes obtaining resolution values from the first image and the second image. In some embodiments, separating high quality data includes obtaining brightness and contrast values from the first image and the second image.

In some embodiments, selecting a common boundary includes interpolating data in the first image and the second image. The method of claim 13 wherein the interpolating data includes interpolating data along a circumference in a cross section of the patient volume. For example, the circumference may be as any circle centered approximately at the center of the blood vessel in FIG. 8. In some embodiments, interpolating data includes interpolating data along a radius of the circumference. In some embodiments, interpolating data comprises interpolating data across A-scan lines and digitized radio frequency (RF) samples. In some embodiments interpolating data includes interpolating data increasing the interpolation resolution for data proximal to the common boundary.

Figure 9:
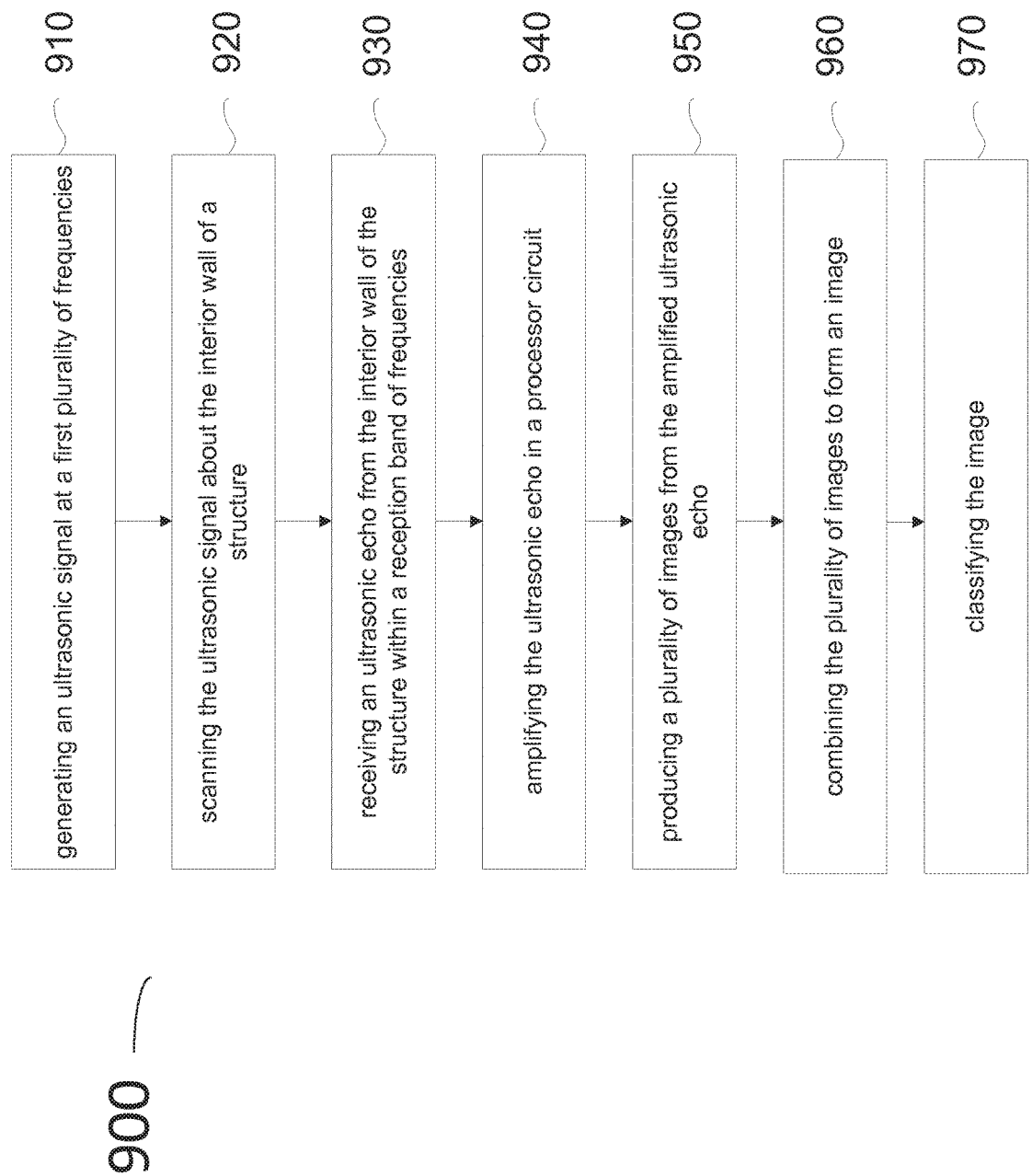
FIG. 9 is a flow chart of a method for multi-frequency imaging according to some embodiments.

FIG. 9 is a flow chart illustrating steps in a method 900 for multi-frequency imaging, according to some embodiments. Method 900 may be performed partially by system 100. According to some embodiments, method 900 may be performed by a control system (e.g., control system 106) using a processor circuit (e.g., processor circuit 156) and a memory circuit (e.g., memory circuit 157) and/or a PIM (e.g., PIM 104) using a processor circuit (e.g. processor circuit 154) and a memory circuit (e.g., memory circuit 155) based on scan data provided by a transducer assembly (e.g., transducer assembly 122 cf. FIG. 1). The transducer assembly may be positioned in the distal end of a catheter positioned inside the lumen of a tissue structure (cf. catheter 102, FIG. 1). In some embodiments, steps in method 900 may be performed by the control system and steps in method 900 may be performed by the PIM.

In some embodiments method 900 displays an IVUS image formulated with data from various IVUS frequencies. For example, the first frequency range, the second frequency range, and the third frequency range described in detail above (cf. FIG. 8). Thus, method 900 combines the desirable benefit of higher resolution from higher frequencies in shallow tissue regions. Method 900 also combines the desirable benefit of deeper depth of focus at lower frequencies in deeper tissue regions. Lower frequencies are also desirable for imaging deeper tissue regions due to larger attenuation at higher frequencies due to scattering losses.

A reconstructed image plane in method 900 may be provided to an external operator in display 108. Thus, the external operator makes a decision of whether to excise a portion of the stenosed segment of the blood vessel using a recanalization tool, based on the reconstructed image plane on display 108. According to some embodiments the recanalization tool may be a physical instrument having a sharp end. In some embodiments, the recanalization tool may be a laser beam susceptible of being directed to a point in the blood vessel and ablate a tissue portion. Further according to some embodiments the recanalization tool may include an abrasive surface that may be rubbed against the target tissue.

Step 910 includes generating an ultrasonic signal at a first plurality of frequencies. Step 910 may further include positioning catheter 102 with its LA substantially aligned with the blood vessel, inside the lumen portion of the blood vessel. Step 920 includes scanning the ultrasonic signal in a predetermined pattern about the interior wall of a structure. In some embodiments the interior wall of a structure is the interior portion of a blood vessel wall including a region of stenosis. The region of stenosis may include a plaque having a calcified portion, a lipid pool, and a necrotic core adjacent to the lipid pool.

Step 930 includes receiving an ultrasonic echo from the interior wall of the structure, within a reception band of frequencies. In some embodiments, a reception band of frequencies in step 930 may include the first plurality of frequencies. In some embodiments, the reception band of frequencies may include harmonic combinations of the first plurality of frequencies. Harmonic combinations of the first plurality of frequencies may include integer multiples of either of the frequencies in the first plurality of frequencies. Furthermore, harmonic combinations of the first plurality of frequencies may include sums of any number of frequencies in the first plurality of frequencies. Step 940 includes amplifying the ultrasonic echo in a processor circuit. Step 940 includes amplifying the ultrasonic echo in the processor circuit. In some embodiments, step 940 may include filtering the ultrasonic echo signal using electronic filters having a band-pass including the second selected frequency. Accordingly, a portion of step 940 may be performed by an ASIC circuit at a distal end of the catheter (e.g., ASIC 144 in FIG. 1B).

Step 950 includes producing a plurality of images from the amplified ultrasonic echo. Accordingly, step 950 may include producing an image for each of the frequencies within the reception band of frequencies in step 930. Producing each image in step 950 may be as described in detail above, with relation to step 850, in method 800. Step 950 includes producing an image from the ultrasonic echo. According to some embodiments, step 950 may be performed partially by the PIM. For example, step 950 may be partially performed by a reconstruction circuit (e.g., reconstruction circuit 250, FIG. 2). In some embodiments, step 950 may be performed partially by the control system. According to some embodiments, step 950 includes producing a 2-dimensional image (2D-image) of a cross section of the blood vessel wall. The cross-section may be substantially parallel to an XY-plane perpendicular to a LA oriented along the blood vessel and the catheter direction (cf. FIG. 1). In some embodiments, step 950 includes producing a 3-dimensional image (3D-image) of the blood vessel wall from a plurality of 2D-images.

Step 960 includes combining the plurality of images from step 950 to form an image. In some embodiments, step 960 may include combining a portion of a first image obtained with a high frequency ultrasound echo with a portion of a second image obtained with a low frequency ultrasound echo. Accordingly, the portion of the first image may be a shallower portion of the tissue structure, and the portion of the second image may be a deeper portion of the tissue structure. Furthermore, the portion of the second image may filter out blood speckle artifacts typically encountered in high frequency ultrasound signal, such as used for the first image. For example, a first portion of an image of a blood vessel obtained at 80 MHz may include the endothelium of the blood vessel, including the border between the blood vessel wall and the lumen. A second portion of an image of a blood vessel obtained at 20 MHz may include portions of necrotic tissue in a plaque, macrophage cells, and muscle cells deeper into the blood vessel wall.

Step 970 includes classifying the image obtained in step 960. Step 970 may be performed by processor circuit 156 and memory circuit 157 in control system 106. In some embodiments, step 970 is performed by processor circuit 156 executing commands, retrieving and storing data, the commands and the data being stored in memory circuit 157. For example, in some embodiments the commands executed by processor circuit 156 in control system 106 may be included in an image characterization code stored in memory circuit 157. The image characterization code may render a characterized tissue component map. In some embodiments, the image characterization application is able to perform a spectral analysis of ultrasound echo information for a blood vessel cross-section. Thus, different plaque components may be determined and distinguished in the characterized tissue map. For example, the characterization application may use a classification criterion including a rule based upon a location of a confluence of necrotic core within the vessel cross-section in relation to a border between the lumen and a plaque.

In some embodiments, a classification criterion may use the thickness of a fibrous cap to determine the vulnerability of a plaque, and the likelihood of plaque rupture and thrombosis. For example, a plaque may be classified as 'vulnerable' to rupture, based on the size, configuration, and nature of its components. A component of a plaque within a blood vessel may be a fibrous cap and a necrotic core. In some configurations a component of a plaque within a vessel may include fat cell tissue and macrophage cells. The nature of a component of a plaque within a vessel may include substances such as elastin, collagen and cholesterol. The viscoelastic properties of the substances and the configuration of the different components included in a plaque within a vessel provide a differentiated acoustic response to the ultrasonic signals in step 910. Thus, interaction of the blood vessel wall with ultrasonic signals in step 910 may produce an image that clearly differentiates the components of the plaque, their nature, and their configuration (size and shape).

The image characterization code may render a characterized tissue component map. In some embodiments, the image characterization application performs a spectral analysis of ultrasound echo information for a vessel cross-section. Thus, different plaque components may be determined and distinguished in the characterized tissue component map. For example, the characterization application may use a classification criterion including a rule based upon a location of a confluence of necrotic core within the vessel cross-section in relation to a border between the lumen and a plaque. A classification criterion may include a rule, based upon a location, in relation to a lumen-plaque border, of confluent necrotic core within the vessel cross-section; and rendering, in response to the classification, a plaque classification associated with the vessel cross-section. For example, a classification criterion may use the thickness of fibrous cap to determine the vulnerability of a plaque, and the likelihood of plaque rupture and thrombosis. Image characterization applications as used in step 970 may be as disclosed in U.S. Pat. No. 7,627,156 entitled "Automated lesion analysis based upon automatic plaque characterization according to a classification criterion," U.S. Pat. No. 7,175,597 entitled "Non-Invasive Tissue Characterization System and Method," and U.S. Pat. No. 6,200,268 entitled "Vascular Plaque Characterization," each incorporated herein by reference in its entirety, for all purposes.

Figure 10:
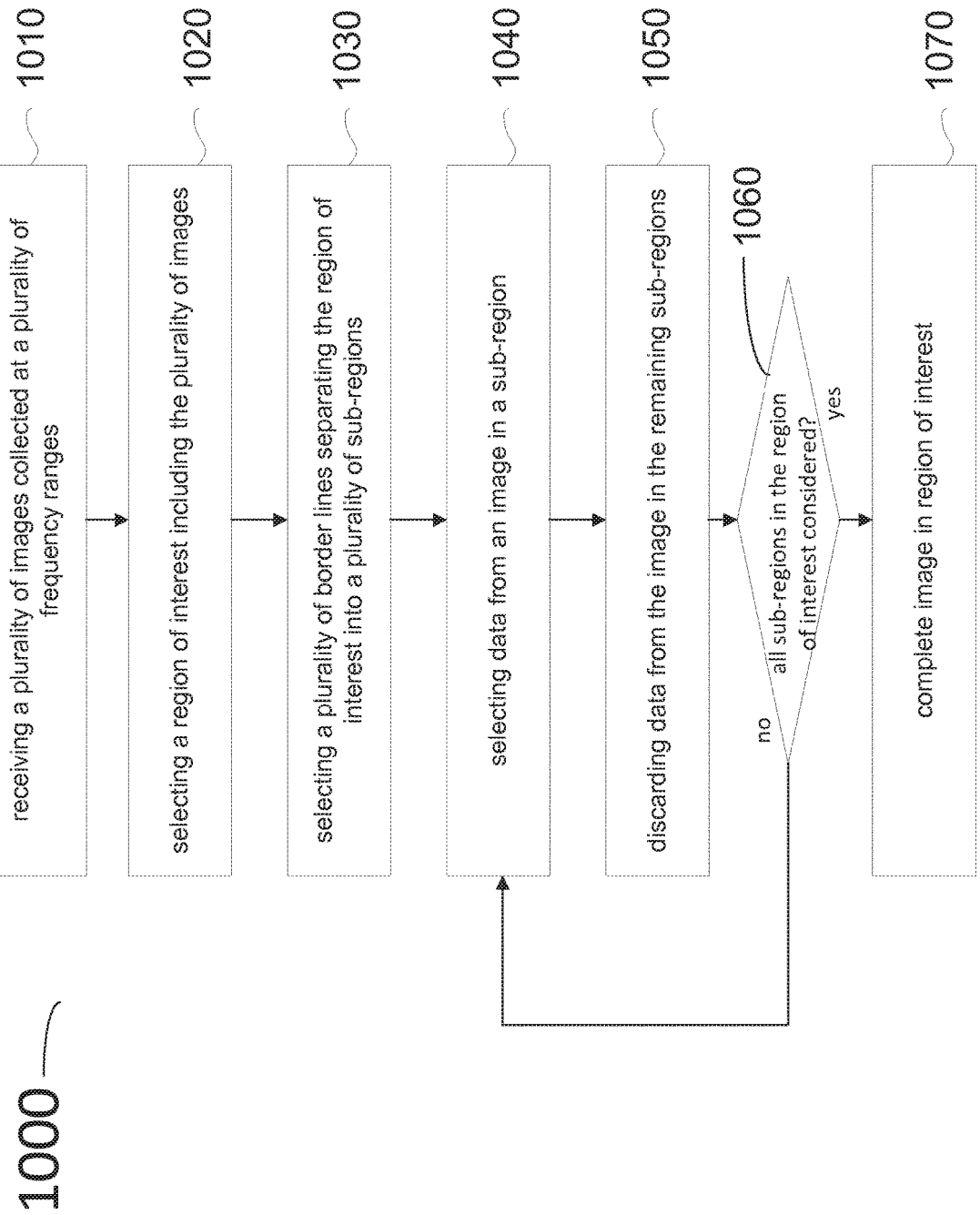
FIG. 10 is a flow chart of a method for combining a plurality of images to form an image, according to some embodiments.

FIG. 10 is a flow chart of a method 1000 for combining a plurality of images to form an image, according to some embodiments. Method 1000 may be performed partially by system 100. According to some embodiments, method 1000 may be performed by a control system (e.g., control system 106) using a processor circuit (e.g., processor circuit 156) and a memory circuit (e.g., memory circuit 157) and/or a PIM (e.g., PIM 104) using a processor circuit (e.g. processor circuit 154) and a memory circuit (e.g., memory circuit 155) based on scan data provided by a transducer assembly (e.g., transducer assembly 122 cf. FIG. 1). The transducer assembly may be positioned in the distal end of a catheter positioned inside the lumen of a tissue structure (cf. catheter 102, FIG. 1). In some embodiments, steps in method 1000 may be performed by the control system and steps in method 1000 may be performed by the PIM. Accordingly, in some embodiments method 1000 may be performed as part of step 960 in method 900, described in detail above (cf. FIG. 9).

Step 1010 includes receiving a plurality of images collected at a plurality of frequency ranges. Step 1020 includes selecting a region of interest including the plurality of images. Step 1030 includes selecting a plurality of border lines separating the region of interest into a plurality of sub-regions. In some embodiments step 1030 includes associating each of the border line with a depth of focus for a frequency selected from the plurality of frequency ranges. Step 1040 includes selecting data from an image in a sub-region. Step 1050 includes discarding data from the image in the remaining sub regions. Step 1060 includes querying whether all sub-regions in the region of interest have been considered. When the answer in step 1060 is yes, step 1070 includes forming an image in the region of interest. When the answer in step 1060 is no, method 1000 is repeated from step 1040.

One of ordinary skill will recognize that components of a device as disclosed herein and steps consistent with methods described herein may be used in multi-modality imaging. For example, in a applications using a combined approach of Optical Coherence Tomography (OCT) and IVUS imaging may benefit from steps as described above in methods 900 and 1000. Indeed, an OCT image may provide accurate information of shallow tissue portions, with higher resolution than IVUS techniques may offer. Likewise, IVUS imaging may provide a high quality data of tissue extending beyond a blood vessel lumen. Thus, the near field OCT image data can be combined with the far field IVUS image data to form a composite image providing enhanced image quality for the inspected tissue.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. A system for imaging a patient volume, comprising:
a processor circuit in communication with an intravascular imaging device and a display, wherein the processor circuit is configured to:
  control the intravascular imaging device to obtain a first image of a blood vessel using a first frequency while the intravascular imaging device is positioned within the blood vessel;
  control the intravascular imaging device to obtain a second image of the blood vessel using a lower, second frequency while the intravascular imaging device is positioned within the blood vessel;
  form a first border line in the first image corresponding to a first depth of focus of the intravascular imaging device at the first frequency, wherein the first border line comprises a closed shape within a cross-section of the blood vessel depicted in the first image;
  identify, based on the first border line, a first depth region of the first image corresponding to the first depth of focus;
  form a second border line in the second image corresponding to a second depth of focus of the intravascular imaging device at the second frequency, wherein the second border line comprises the closed shape within the cross-section of the blood vessel depicted in the second image, wherein the first border line and the second border line are distinct from one another because of the first border line being formed in the first image and the second border line being formed in the second image;

identify, based on the second border line, a second depth region of the second image corresponding to the second depth of focus, wherein the second depth region is farther from the intravascular imaging device than the first depth region, and wherein no portion of the second depth region overlaps with the first depth region;

combine the first depth region of the first image and the second depth region of the second image to form a composite image of the blood vessel; and output the composite image to the display.

2. The system of claim 1, wherein the first frequency is a harmonic of the second frequency.

3. The system of claim 1, wherein the first depth region and the second depth region include high resolution image regions of a lumen and a lumen boundary of the blood vessel.

4. The system of claim 1, wherein the processor circuit is configured to:

discard, from the first image, a third depth region that does not overlap with the first depth region; and discard, from the second image, a fourth depth region that does not overlap with the second depth region, wherein the first depth region is positioned on a first side of the first border line and the third depth region is positioned on a second side of the first border line, and wherein the second depth region is positioned on a second side of the second border line and the fourth depth region is positioned on a first side of the second border line.

5. The system of claim 1, wherein the patient volume includes an interior wall of the blood vessel.

6. The system of claim 1, further comprising the intravascular imaging device.

7. The system of claim 6, wherein the intravascular imaging device comprises at least one of an intravascular ultrasound (IVUS) device or an optical coherence tomography (OCT) device.

8. The system of claim 1, wherein the first border line surrounds the imaging device, and wherein the second border line surrounds the imaging device.

* * * * *